United States Patent [19]
DePriest et al.

[11] 4,017,349
[45] Apr. 12, 1977

[54] APPARATUS FOR MANUFACTURING LARGE DISPOSABLE SPECIALTY DRAPES

[75] Inventors: Donald R. DePriest; Bobby C. Brandon, both of Columbus, Miss.

[73] Assignee: Humboldt Products Corporation, Columbus, Miss.

[22] Filed: Mar. 28, 1975

[21] Appl. No.: 563,180

Related U.S. Application Data

[63] Continuation of Ser. No. 329,144, Feb. 2, 1973, abandoned.

[52] U.S. Cl. .............................. 156/361; 156/253; 156/510; 156/552; 156/578
[51] Int. Cl.² ............... B65C 11/00; B65H 25/00
[58] Field of Search .......... 156/361, 511, 513, 514, 156/510, 541, 552, 554, 562, 578, 253; 83/208, 353, 508

[56] References Cited

UNITED STATES PATENTS

| | | | |
|---|---|---|---|
| 1,983,323 | 12/1934 | Stokes | 156/514 |
| 2,284,872 | 6/1942 | Jaeger et al. | 156/514 |
| 2,720,248 | 10/1955 | Kipnis | 156/516 |
| 3,177,749 | 4/1965 | Best et al. | 83/208 |
| 3,232,808 | 2/1966 | Dries et al. | 156/253 |
| 3,620,114 | 11/1971 | Chudyk | 83/208 |

Primary Examiner—Charles E. Van Horn
Assistant Examiner—M. G. Wityshyn
Attorney, Agent, or Firm—James N. Dresser

[57] ABSTRACT

Apparatus for manufacturing large, disposable specialty drapes such as laparotomy sheets. Strips of stock material are automatically drawn from a supply and glued together to form the required width. A reinforcement patch is attached and then a fenestration cut through the patch and the underlying stock material. Subsequently, the fenestrated stock material is cut off to provide the finished sheet. The work stations at which the reinforcement patch is applied, the fenestration cut and the finished sheet cut off are spaced so that these operations can be performed simultaneously on different sheets in a line. A control unit is provided to control these operations simultaneously.

11 Claims, 12 Drawing Figures

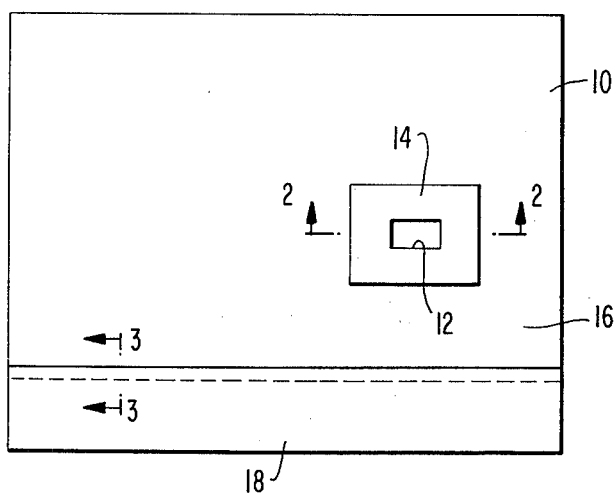
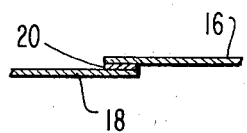
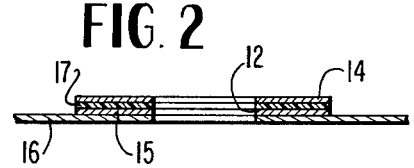
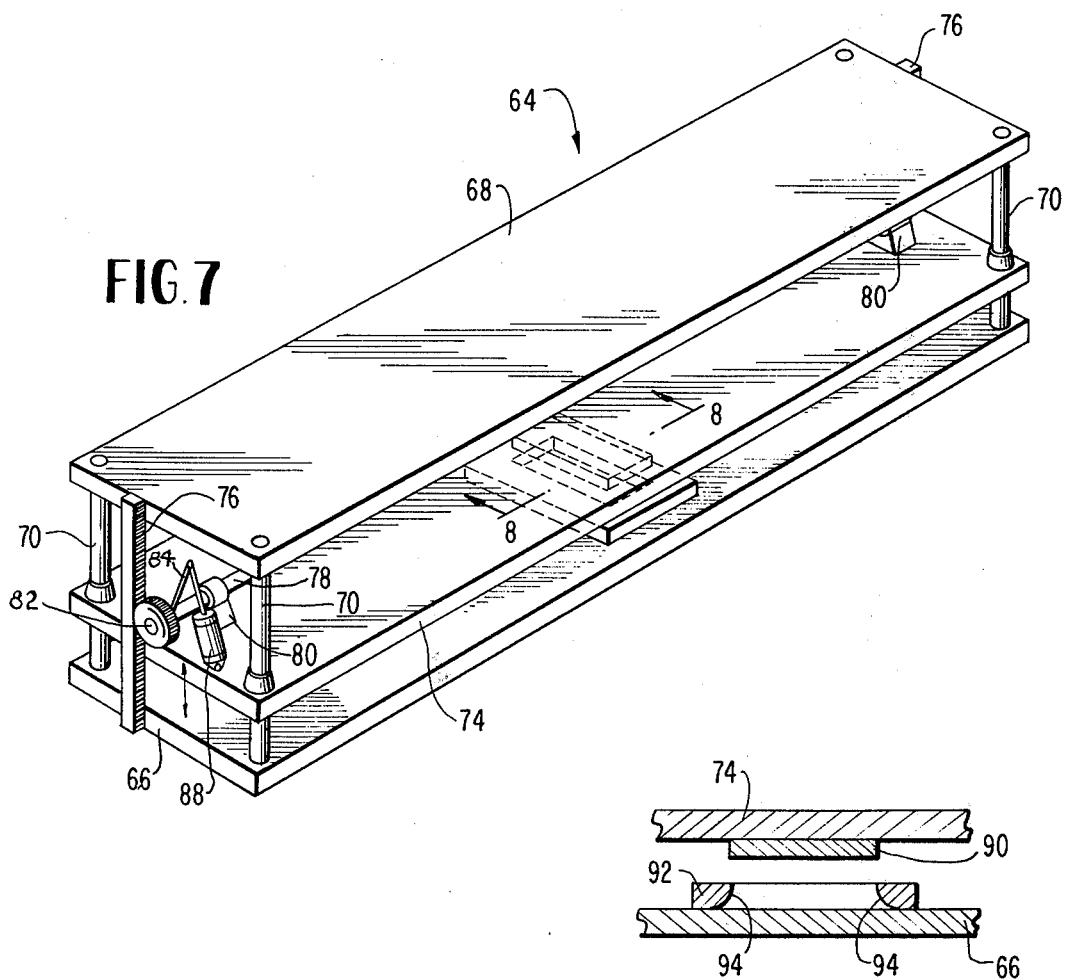
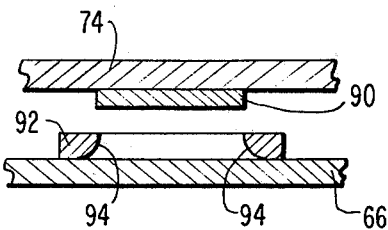

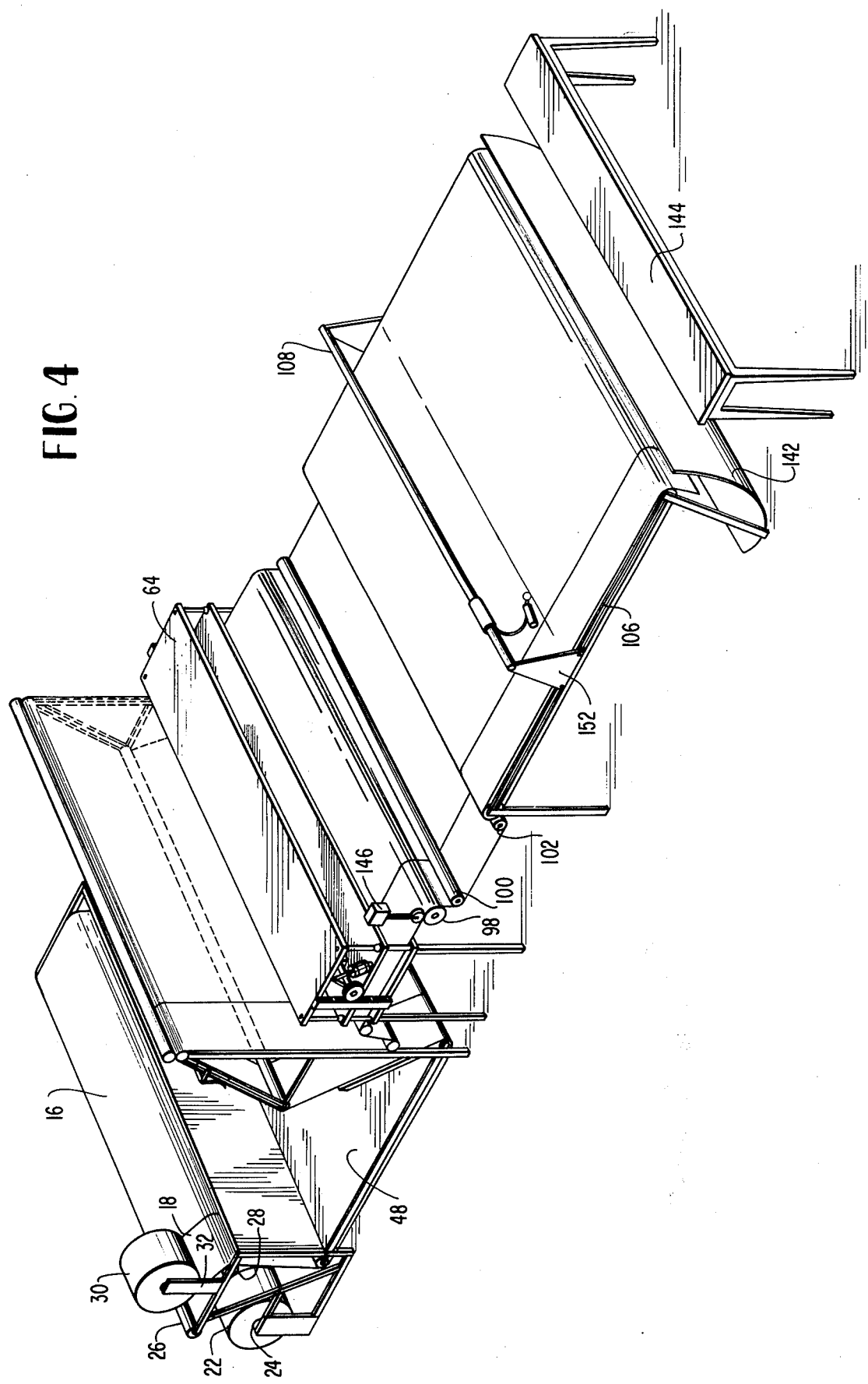

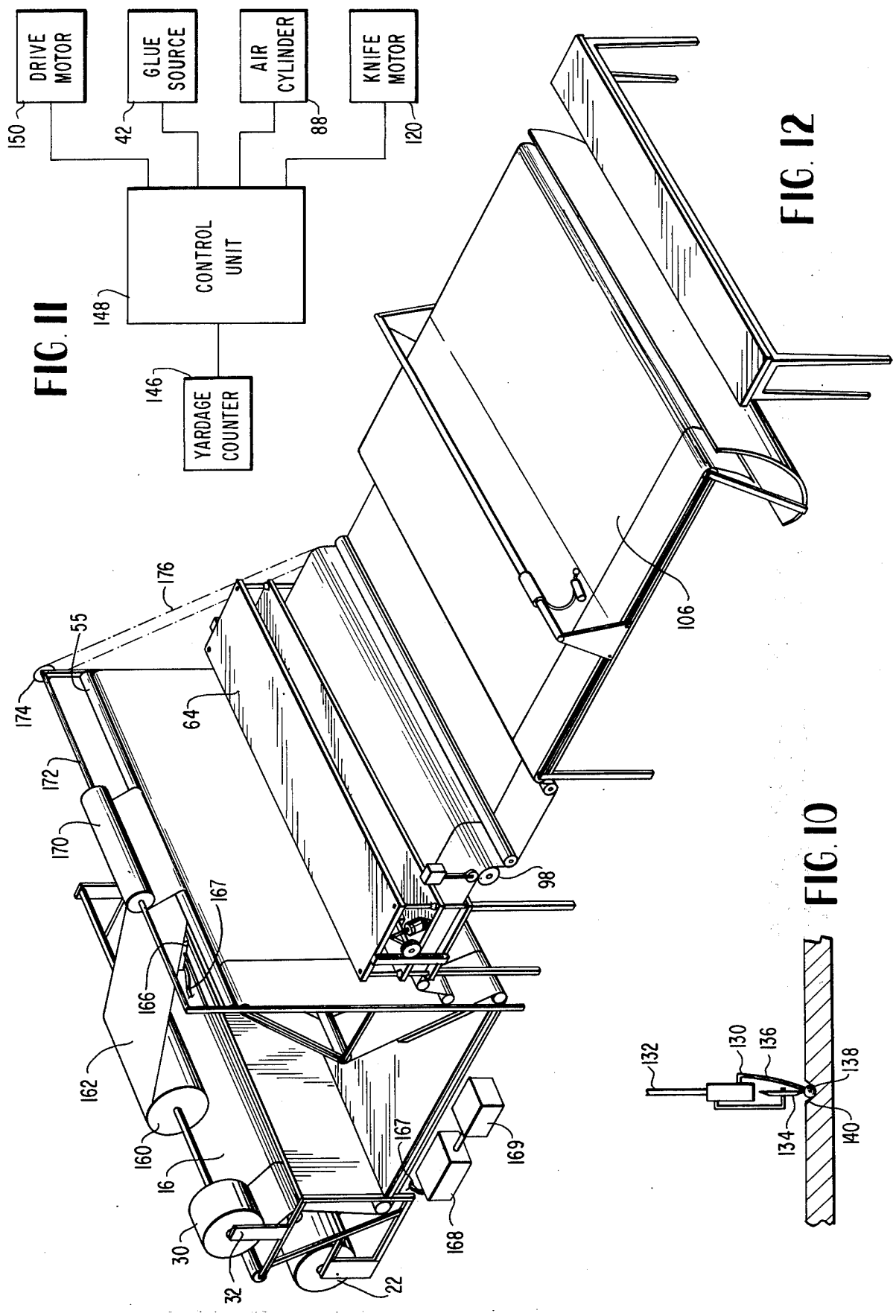

APPARATUS FOR MANUFACTURING LARGE DISPOSABLE SPECIALTY DRAPES

This is a continuation, of application Ser. No. 329,144, filed Feb. 2, 1973, and now abandoned.

The present invention pertains to large disposable specialty drapes. More particularly the present invention pertains to apparatus for manufacturing large, disposable specialty drapes such as laparotomy sheets or other surgical drapes.

Large, disposable drapes or sheets are utilized in a variety of applications. By way of example, such drapes or sheets are frequently utilized in hospital operating rooms to cover a patient undergoing surgery. These surgical drapes are provided in a variety of styles to meet the requirements of different operating procedures. Generally, such surgical sheets are very large, for example, having a width in the order of 87 inches and a length in the order of 130 inches. In addition, the surgical sheets are generally provided with an opening or fenestration at a location determined by the surgical procedure involved. The fabrication of such large, disposable specialty drapes is complicated by the fact that the stock material from which they are made is generally available, only in widths more narrow than the desired width of the finished sheets. In addition, the location of the fenestration is quite exact. Such sheets have been made in the past by techniques such as cutting two or three relatively narrow pieces of stock material to the desired length and with the desired fenestration, spreading them out on a large table, and glueing them together. This, of course, involves numerous handling steps which makes the manufacturing process both slow and subject to error.

The present invention is an apparatus for automatically manufacturing large, disposable specialty drapes, such as surgical sheets or drapes, in which the number of manual steps is reduced to a minimum. In accordance with the present invention, the stock material is automatically fed through a series of work stations at which the necessary manufacturing operations are performed.

If the desired finished sheet is of a width greater than that in which the stock material is available, the necessary number of widths of stock material are unwound from supply rolls with sufficient overlap, and an adhesive is applied. The widths of stock material are thus automatically joined as they pass through the apparatus of the present invention. The stock material of the desired width is then passed to a second work station at which a reinforcement patch is applied. From that station, the material passes to a cutting work station at which the desired fenestration is cut. The material then proceeds to another work station at which the material is cut at the proper length to provide the finished sheet. From there the sheet proceeds for folding and packaging.

These and other aspects and advantages of the present invention are more apparent in the following detailed description and claims, particularly when considered in conjunction with the accompanying drawings in which like parts bear like reference numerals. In the drawings:

FIG. 1 is a plan view of a laparotomy sheet illustrative of the large, disposable specialty sheets or drapes which might be manufactured on apparatus in accordance with the present invention;

FIGS. 2 and 3 are fragmentary sectional views taken respectively along line 2—2 and along line 3—3 of FIG. 1;

FIG. 4 is a perspective view of apparatus in accordance with the present invention for manufacturing large, disposable specialty drapes;

FIG. 7 is a perspective view of a fenestration cutting device suitable for use in the apparatus of FIG. 4 in accordance with the present invention;

FIG. 8 is a fragmentary sectional view taken along line 8—8 of FIG. 7;

FIG. 10 is a fragmentary sectional view taken along line 10—10 of FIG. 9;

FIG. 11 is a block diagram illustrating connection of control circuitry for apparatus in accordance with the present invention; and FIG. 12 is a perspective view of a modified embodiment of apparatus in accordance with the present invention.

Figure 5:
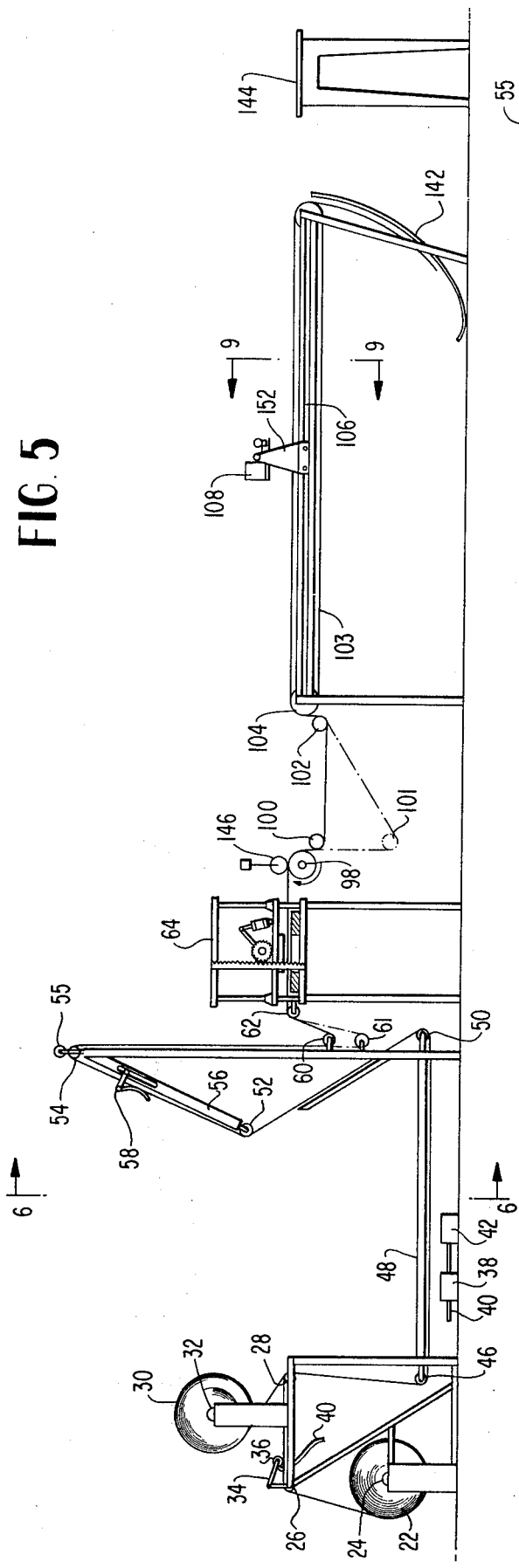
FIG. 5 is an elevational view of the apparatus of FIG. 4.

FIG. 1 depicts a laparotomy sheet 10 typical of the large disposable sheet or drapery items which can be manufactured on an apparatus in accordance with the present invention. Sheet 10, by way of example, might have a width in the order of 87 inches and a predetermined length in the order of 130 inches, although these dimensions might vary depending upon the particular surgical procedure with which sheet 10 is to be utilized. Some surgical drapes might have a width closer to 70 inches. Others might have a length in the order of 102 inches. Sheet 10 is used to cover the patient as he reclines on the operating table. A fenestration 12 is made through sheet 10 at the predetermined location at which the operating procedure is to be performed. Fenestration 12 will be of a size dependent upon the surgical procedure with which sheet 10 is to be utilized and, for example, might have a width in the order of eight inches and a length in the order of twelve inches. A reinforcement patch 14 is attached by an adhesive 15 over the area surrounding the fenestration 12, and the fenestration is provided through both layers of material, as depicted in FIG. 2.

If sheet 10 is of a width greater than that available in the stock material from which the sheet is made, then sheet 10 is manufactured from two or more strips of stock material. As illustrated in FIG. 3, the edges of strips 16 and 18 overlap, for example a distance in the order of one inch, and strips 16 and 18 are joined in this area by a suitable adhesive 20.

The stock material of strips 16 and 18 is preferably a nonwoven material suitably treated to be water repellant. Strips 16 and 18 can be joined by any suitable liquid adhesive 20, for example a water base, latex adhesive. Reinforcement patch 14, which for example might have a width in the order of 33 inches and a length in the order of 44 inches, is similarly a water repellant nonwoven material, and preferably in addition has a layer 17 of fluid impermeable material, such as polyethylene which has been suitably treated to be anti-static, laminated on its underside, between the nonwoven material of patch 14 and the nonwoven material of stock material 16. Patch 14 thus makes the area around fenestration 12 totally fluid impermeable.

Patch 14 is held in place by a water base, pressure sensitive latex adhesive 30.

Figure 6:
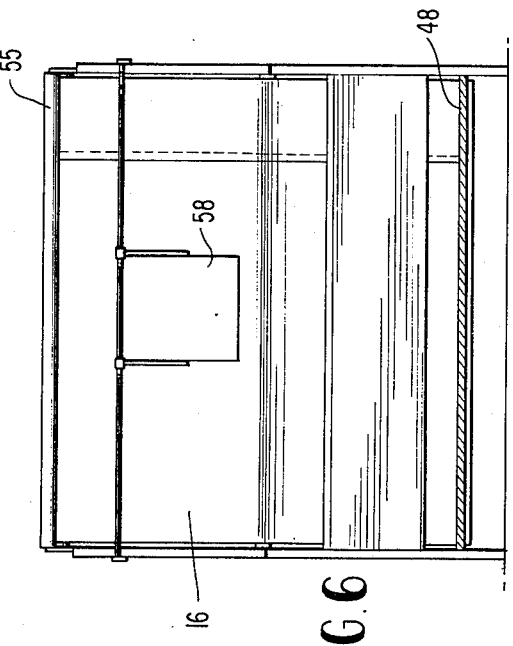
FIG. 6 is a sectional view taken along line 6—6 of FIG. 5.

FIGS. 4, 5, and 6 depict apparatus in accordance with the present invention for manufacturing sheets such as sheet 10. A roll 22 of stock sheet material 16 is mounted on unwind stand or holder 24, and the stock material 16 from roll 22 passes over roller 26 and roller 28. A second roll 30 of stock sheet material 18 is mounted on stand or holder 32 to unwind adjacent the stock material 16 from roll 22 with an overlap in the order of, for example, 1 inch. Support arm 34 holds glue head 36 to apply a suitable liquid adhesive to the overlapped one inch of stock material 16. The liquid adhesive is provided from a supply 38 through hose 40 to glue head 36 under pressure from pneumatic source 42. The adhesive is applied to stock material 16 just before it contacts stock material 18, and the pressure applied to the two layers of material as they pass over roller 28 is sufficient to cause the adhesive to join them.

From roller 28 the sheet of stock material passes about roller 46, then beneath support platform 48, and about roller 50. From roller 50 the stock material moves upward and about rollers 52 and 54. Platform 48 and rollers 52 and 54 define a work station for the applying of reinforcement patch 14. In the embodiment of the present invention depicted in FIGS. 5 and 6, an operator stands on platform 48, and support member 56 is mounted between rollers 52 and 54 and preferably is angled slightly, as depicted in FIG. 5, so that as the stock material passes across member 56, it is inclined slightly away from the operator on platform 48. An alignment and positioning guide 58 is mounted on member 56 to indicate the position on the sheet material at which the operator at station 48 is to align and apply a reinforcing patch 14.

When a reinforcement patch 14 is to be applied to stock material 16 on the apparatus of FIG. 5, movement of the stock material through the apparatus is stopped, and the operator on platform 48 applies adhesive to a patch, for example by passing a pre-cut patch through a glue machine, such as available under the trademark Potdevin, to apply a thin controlled layer of adhesive 15 to the entire surface of the patch. The operator then places the patch 14 on stock material 16 in the location indicated by positioning guide 58. When the stock material and patch move from support member 56, they pass between rollers 54 and 55, and the resulting pressure assures that patch 14 is securely adhered to stock material 16.

From roller 54 the material passes downward and around rollers 60 and 62 to fenestration cutting station 64. FIGS. 7 and 8 illustrate apparatus suitable for the fenestration cutting station 64. Lower member 66 and upper member 68 are fixedly mounted on rods 70. Center member 74 is slidingly mounted on rods 70 between lower member 66 and upper member 68. Racks 76 are mounted at the ends of cutting station 64 between lower member 66 and upper member 68. Shaft 78 is rotatably mounted to center member 74 by means of mounts 80. A pinion 82 is mounted on each end of shaft 78 to engage the racks 76. Linkage 84 couples shaft 78 to air cylinder 88 which is mounted on center member 74. Movement of linkage 84 under control of air cylinder 88 rotates shaft 78 to cause center member 74 to be raised or lowered. Other suitable means of raising and lowering member 74 could, of course, be provided.

A peened anvil punch press is positioned on center member 74 and lower member 66. Hammer member 90 is mounted on the lower surface of center member 74, while anvil member 92 is mounted opposite hammer member 90 and on the upper surface of lower member 66. Anvil member 92 includes beveled edges 94, while hammer member 90 has clean, non-beveled edges. Hammer member 90 is preferably of a hard steel, and anvil member 92 is preferably of a slightly softer metal. The stock material 16 has a thickness in the order of seven mils. Anvil 92 might have a thickness in the order of 3 inches. Punch 90 only goes into the opening of anvil 92 about one-half inch. Therefore, there are two-and-one-half inches of depth in which the portions of paper removed from stock material 16 and patch 14 can accumulate. This is generally about enough catch room for a production run in the order of 500 sheets. Alternatively, if desired, an opening can be provided in lower member 66 to conform with the outline of the opening through anvil member 92 so that the portion of the material removed as each fenestration is cut can fall from cutting station 64. However, with no opening through lower member 66, different hammers and anvils can be utilized to permit cutting different fenestrations for various types of surgical drapes and without weakening lower member 66.

Figure 9:
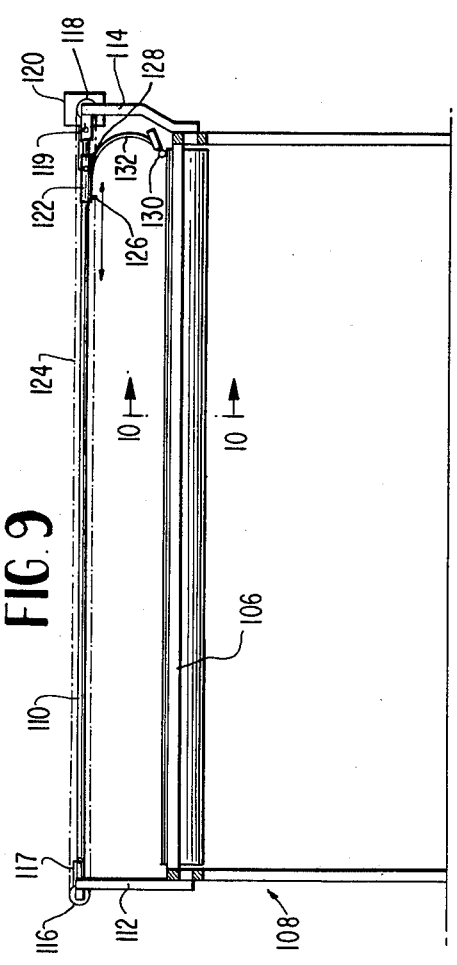
FIG. 9 is a sectional view taken along line 9—9 of FIG. 5.

From fenestration cutting station 64 the sheet material passes about power drum 98 and guide rollers 100 and 102. From there the material passes onto conveyor 103 which conveys it across work table 106. Power drum 104 drives conveyor 103. An automatic knife 108 is positioned on work table 106 to cut the sheet material at the desired length for the particular specialty drape being manufactured. FIGS. 9 and 10 illustrate an automatic knife suitable for automatic knife 108. Support rod 110 is mounted by members 112 and 114 at the desired location, transverse the path of travel of the stock material on work table 106. Mounting member 112 also supports gear wheel 116 and limit switch 117, while mounting member 114 supports gear wheel 118, limit switch 119, and motor 120. Pipe 122 is mounted on support rod 110. Drive chain 124 passes from attachment 126 on one end of the lower surface of pipe 122, about gears 116 and 118 and connects to attachment 128 on the second end of the lower surface of pipe 122. Motor 120 drives gear 118. Consequently, activation of motor 120 causes pipe 122 to move across support rod 110. Knife 130 is supported by support member 132 from pipe 122. By way of illustration, knife 130 can be a rotary knife such as is available under the trademark Chickadee. As seen in FIG. 10, knife 130 has a rotary wheel blade 134 and a support blade 136. Ball 138 is rotatably attached to the end of support blade 136 to ride in groove 140 on work table 106. As wheel blade 134 rotates, its cutting edge contacts the cutting edge of support blade 136 with a cutting action. Preferably, support member 132 is formed of a material such as a spring steel leaf which applies a slight downward pressure to knife 130.

When a finished drape is to be cut from fenestrated stock material by automatic knife 108, the movement of the stock material is stopped, and motor 120 is activated. As a consequence, pipe 122 moves across the width of surface 106, moving knife 130 with it. Ball 138 and a portion of support blade 136 are beneath the stock material while cutting wheel 134 is above it. Therefore, as rotary knife 130 moves across surface 106, the stock material is cut. When pipe 122 comes into the vicinity of limit switch 117, the limit switch activates circuitry reversing the energization to motor 120, and so the motor reverses the direction of gear 118. Consequently, pipe 122 is moved back across rod 110, causing knife 130 to return to its starting position. When pipe 122 approaches limit switch 119, that limit switch causes circuitry to again reverse the direction of energization of motor 120, readying the cutting device for the next cutting operation.

Once the desired sheet is cut, the sheet continues to move along conveyor 103 to accumulator 142, which is provided to cause the sheet to adopt a fan fold as it emerges from surface 106. An operator is positioned adjacent accumulator 142 to pick up sheet 10 as it emerges from knife 108 and to fold it in the desired manner. Preferably a support surface or table 144 is provided for use by the operator in folding the sheet.

A linear yardage counter 146 is mounted, for example adjacent power drum 98, to measure the yardage of material as it passes. Yardage counter 146 is connected to control unit 148, as depicted in FIG. 11. Control unit 148 monitors the yardage indication from yardage counter 146 and activates the necessary components at appropriate intervals. Thus, when control unit 148 determines that yardage equivalent to the length of one sheet has passed, it stops drive motor 150 which drives power drums 98 and 104. In addition, unit 148 cuts off pneumatic source 42 to stop the flow of liquid adhesive. Control unit 148 then activates air cylinder 88 of fenestration cutting device 64 and motor 120 of automatic knife 108. During this same period of time the operator positioned on support 48 applies a reinforcement patch to the sheet material at surface 56, and the operator adjacent accumulator 142 removes the newly cut sheet 10 for folding. Control unit 148 can include a manually operated switch permitting an operator to start drive motor 150 and pneumatic source 42 after the reinforcement patch 14 is applied, the cutting operations completed, and the newly finished sheet 10 removed for folding. Alternatively, control unit 148 can include a timer to restart motor 150 and source 42 automatically after an interval sufficient for these operations to take place, for example an interval in the order of 15 seconds.

The threading of sheet material 16 through the apparatus as depicted in solid line in FIG. 5, is appropriate when drapes or sheets of a particular length, for example 102 inches, are being manufactured. This threading results in an integral number of sheet lengths being laid out along the path of travel between member 56, at which the reinforcement patches 14 are applied, and fenestration cutting station 64. In addition, this threading makes the distance from fenestration cutting station 64 to knife 108 equal to the distance from fenestration 12 to an end of sheet 10 plus an integral multiple of the sheet length (zero being an integer) so that the end of a sheet is at knife 108 when fenestration locations are at member 56 and at station 64. Consequently, when movement of the stock material is stopped, the stock material is properly positioned for the simultaneous occurence of all three operations: applying a reinforcement patch 14 at member 56, cutting a fenestration 12 through a previously applied patch 14 at cutting station 64, and cutting a previously fenestrated sheet 10 from the stock material 16 at knife 108. If a different length sheet 10 is to be manufactured, the path threading is altered appropriately. Thus, for example, if a 130 inch sheet is being manufactured, the stock material is threaded about roller 61 rather than about roller 60 and is threaded about roller 101 rather than about roller 100. Alternatively, rollers 60 and 100 can be adjustable to move to the positions 61 and 101, respectively, for the longer sheets. Preferably, knife 108 is mounted to surface 106 by means such as bracket 152 which permits longitudinal adjustment of knife 108 to accommodate small variations in sheet length.

Should stock material be available in a width suitable for the finished drape, then of course, it is not necessary to glue the two layers of stock material. In such event, if desired, the supply roll 22 can be positioned at roller 50 to supply the stock material to surface 56 at which the fenestration reinforcement patch is applied. If desired, of course, the finished sheet could be formed from three or more panels of material obtained from separate supply rolls and glued together in a manner similar to that depicted in FIGS. 4 and 5.

Preferably in accordance with the present invention, the application of the reinforcement patches 14 is also automated. FIG. 12 illustrates one means for accomplishing this. Support member 32, which supports supply roll 30 of the stock material 18, also supports a supply roll 160 of a backing paper 162 having reinforcement patches 14 attached thereto at the desired intervals. The backing paper 162 is fed from roll 160 and around roller 55. A glue head 166 is positioned between supply roll 160 and roller 55 to apply adhesive to each reinforcement patch 14. Glue head 166 is supplied via hose 167 from adhesive source 168 which is activated by a pneumatic source 169 under control of control unit 148. From roller 55, backing paper 162 is fed to a take-up roll 170 on shaft 172. Gear 174 is mounted on one end of shaft 172 and is coupled by chain 176 to power drum 98. Under the control of control unit 148, adhesive supply 168 provides adhesive to glue head 166 as each reinforcement patch 14 passes the glue head. The reinforcement patches 14 then contact sheet material 16 at roller 54. The reinforcement patches adhere to sheet material 16 while the backing paper 162 passes up to take-up roll 170. As an alternative, glue head 166 can be positioned and controlled to apply adhesive to those locations on sheet 16 at which reinforcement patches 14 are to be applied. Accordingly, the reinforcement patches are applied at the desired locations. Support platform 48 is not required in this embodiment but can be included if desired. FIG. 12 is thus illustrative of a manner in which attachment of reinforcement patch 14 can be automated.

Supply rolls 22 and 30, fenestration cutting station 64, and surface 106 are supported on suitable support framework, for example, a frame made of 2 inch × 2 inch × ¼ inch angle iron. Platform 48 can be a sheet of ¾ inch plywood, for example. Other suitable frames and platforms might be substituted for these.

Power drum 98 and power drum 104 provide two drive sources to move the stock material through the apparatus. With suitable stock material, a single drive source might be satisfactory. However, if the tensile strength of the stock material is low, two drive sources are preferable to assure that the stock material is not torn.

Although the present invention has been described with reference to a preferred embodiment, numerous modifications and rearrangements could be made, and still the result would be within the scope of the invention.

What is claimed is:

1. Apparatus for forming large, disposable specialty drapes having a predetermined length from a first end thereof to a substantially parallel second end thereof and having a fenestration a predetermined distance from the first end thereof, said apparatus comprising:
   a. holding means for holding a plurality of rolls of stock material positioned to overlap as the stock material is withdrawn therefrom;
   b. adhesive supply means for applying adhesive to the area of overlap of stock material taken from at least one roll thereof;
   c. means for applying pressure to the area of overlap of stock material taken from said plurality of rolls after adhesive has been applied to at least one roll thereof;
   d. means defining a first work station;
   e. alignment means for aligning a reinforcement patch on stock material passing the first work station from the holding means;
   f. punch means for cutting a fenestration through reinforced stock material passing the punch means from the first work station;
   g. support means for supporting said holding means, said first work station defining means, said alignment means, and said punch means and including guide means defining a path from said holding means, beneath said first work station defining means, and over said alignment means, permitting an operator positioned at the first work station access to said alignment means, said guide means being adjustable to permit adjustment of the length of the path to accommodate large disposable specialty drapes having various predetermined lengths and predetermined distances;
   h. knife means for cutting large, disposable specialty drapes from fenestrated stock material, said knife means separated from said punch means by a distance along the path equal to the predetermined distance plus an integral multiple of the predetermined length;
   i. drive means for moving stock material along the path from a supply thereof at said holding means; and
   j. control means for intermittently deactivating said drive means and said adhesive supply means and activating said punch means and said knife means, said control means including linear measuring means for measuring the length of stock material moving on the path and a control unit responsive to measurement by said linear measuring means of the present length of stock material for deactivating said drive means and activating said punch means and said knife means.

2. Apparatus as claimed in claim 1 in which said first work station defining means includes a first support member for supporting an operator and a second support member for supporting stock material as the stock material moves along the path, said second support member supporting the stock material in an inclined orientation with respect to an operator on said first support member and in which said alignment means comprises a positioning guide connected to said second support member for indicating the position on stock material at the first work station at which a reinforcement patch is to be applied.

3. Apparatus as claimed in claim 1 in which said alignment means includes means for automatically supplying a reinforcement patch into juxtaposition with stock material moving on the path and means for applying an adhesive on at least one of the reinforcement patch and the stock material, and in which said first work station defining means includes means for applying pressure to a reinforcement patch in juxtaposition with stock material after the adhesive has been applied.

4. Apparatus as claimed in claim 1 in which said knife means comprises a rotary knife and means for moving said rotary knife across the path.

5. Apparatus as claimed in claim 1 in which said guide means includes a plurality of rollers defining a plurality of paths of different lengths to permit threading of stock material therethrough in any of a plurality of selected paths corresponding with various predetermined lengths and predetermined distances.

6. Apparatus as claimed in claim 5 in which at least some of said rollers are adjustable to permit adjustment of the length of the path.

7. Apparatus as claimed in claim 1 in which said control means further includes manual switch means operable when said drive means is deactivated for activating said drive means.

8. Apparatus as claimed in claim 1 in which said control means includes timer means for automatically activating said drive means after said drive means has been deactivated a preset time.

9. Apparatus for forming large, disposable specialty drapes having a predetermined length from a first end thereof to a substantially parallel second end thereof and having a fenestration a predetermined distance from the first end thereof, said apparatus comprising:
   a. holding means for holding a plurality of rolls of stock material positioned to overlap as the stock material is withdrawn therefrom;
   b. adhesive supply means for applying adhesive to the area of overlap of stock material taken from at least one roll thereof;
   c. means for applying pressure to the area of overlap of stock material taken from said plurality of rolls after adhesive has been applied to the at least one roll thereof;
   d. means defining a first work station;
   e. alignment means for aligning a reinforcement patch on stock material passing the first work station from the holding means;
   f. means for applying pressure to a reinforcement patch on stock material passing from the first work station to secure the reinforcement patch to the stock material;
   g. punch means for cutting a fenestration through reinforced stock material passing the punch means from the first work station, said punch means including a hammer member and an anvil member, means for fixedly supporting said anvil member, means for movably supporting said hammer member in a horizontally fixed, vertically movable manner, and means for vertically moving said hammer member into contact with said anvil member;
   h. support means for supporting said holding means, said first work station defining means, said alignment means, and said punch means and including a plurality of rollers defining a plurality of alternative paths of different lengths from said holding means, beneath said first work station defining means, and over said alignment means for passage of disposable stock material along the paths, while permitting an operator positioned at the first work station access to said alignment means, with said alignment means and said punch means separated along the paths by a distance equal to an integral multiple of the predetermined length, with at least some of the rollers defining the paths to be between said hammer member and said anvil member and with at least some of said rollers adjustable to permit adjustment of the length of the paths to accommodate large, disposable specialty drapes having various predetermined lengths and predetermined distances;

i. knife means for cutting large disposable specialty drapes from fenestrated stock material and including a rotary knife, guide means, a rod, means for mounting said rod adjacent said support means and transverse the paths and separated from said punch means by a distance along the paths equal to the predetermined distance plus an integral multiple of the predetermined length, suspension means for slidably suspending said rotary knife from said rod, and motor means for sliding said suspension means along said rod and across the paths, said guide means cooperating with said rollers to guide said rotary knife in a straight line across the paths;

j. drive means for moving stock material along the paths from a supply thereof at said holding means; and k. control means for intermittently deactivating said drive means and said adhesive supply means and activating said punch means and said rotary knife means, said control means including linear measuring means for measuring the length of stock material moving on the paths, a control unit responsive to measurement by said linear measuring means of the preset length of stock material for deactivating said drive means and said adhesive supply means and activating said punch means and said rotary knife means, timer means for automatically activating said drive means and said adhesive supply means after said drive means and said adhesive supply means having been deactivated a preset time, and manual switch means operable when said drive means and said adhesive supply means are deactivated, for activating said drive means and said adhesive supply means.

10. Apparatus as claimed in claim 9 in which said first work station defining means includes a first support member for supporting an operator and a second support member for supporting stock material as the stock material moves along the paths, said second support member supporting the stock material in an inclined orientation with respect to an operator on said first support member and in which said alignment means comprises a positioning guide connected to said second support member for indicating the position on stock material at the first work station at which a reinforcement patch is to be applied.

11. Apparatus as claimed in claim 9 in which said alignment means includes means for automatically supplying a reinforcement patch into juxtaposition with stock material moving on the paths and means for applying an adhesive on at least one of the reinforcement patch and the stock material.

* * * * *